United States Patent
Pibiri et al.

(10) Patent No.: US 11,203,578 B2
(45) Date of Patent: Dec. 21, 2021

(54) OXADIAZOLE DERIVATIVES FOR THE TREATMENT OF GENETIC DISEASES DUE TO NONSENSE MUTATIONS

(71) Applicants: UNIVERSITA' DEGLI STUDI DIPALERMO, Palermo (IT); FONDAZIONE PER LA RICERCA SULLA FIBROSI CISTICA—ONLUS, Verona (IT)

(72) Inventors: Ivana Pibiri, Palermo (IT); Andrea Pace, Palermo (IT); Marco Tutone, Palermo (IT); Laura Lentini, Palermo (IT); Raffaella Melfi, Palermo (IT); Aldo Di Leonardo, Palermo (IT)

(73) Assignees: UNIVERSITA'DEGLI STUDI DIPALERMO, Palermo (IT); FONDAZIONE PER LA RICERCA SULLA FIBROSI CISTICA—ONLUS, Verona (IT)

( * ) Notice: Subject to any disclaimer, the term of this patent is extended or adjusted under 35 U.S.C. 154(b) by 0 days.

(21) Appl. No.: 16/770,240

(22) PCT Filed: Nov. 20, 2018

(86) PCT No.: PCT/EP2018/081850
§ 371 (c)(1),
(2) Date: Jun. 5, 2020

(87) PCT Pub. No.: WO2019/101709
PCT Pub. Date: May 31, 2019

(65) Prior Publication Data
US 2021/0002238 A1    Jan. 7, 2021

(30) Foreign Application Priority Data
Nov. 23, 2017   (IT) .................. 102017000134511

(51) Int. Cl.
*C07D 271/07*   (2006.01)

(52) U.S. Cl.
CPC ................. *C07D 271/07* (2013.01)

(58) Field of Classification Search
CPC .................................................. C07D 271/07
See application file for complete search history.

(56) References Cited

U.S. PATENT DOCUMENTS

2017/0204073 A1   7/2017 Almstead et al.

FOREIGN PATENT DOCUMENTS

| WO | 2006044456 A1 | 4/2006 |
|---|---|---|
| WO | 2006044502 A2 | 4/2006 |
| WO | 2006044503 A2 | 4/2006 |
| WO | 2006044505 A2 | 4/2006 |
| WO | 2006044682 A1 | 4/2006 |
| WO | 2006110483 A1 | 10/2006 |
| WO | 2008045566 A1 | 4/2008 |
| WO | 2008130370 A1 | 10/2008 |
| WO | 2011072281 A1 | 6/2011 |
| WO | 2014085490 A1 | 6/2014 |
| WO | 2015134711 A1 | 9/2015 |
| WO | 2015188037 | 12/2015 |

OTHER PUBLICATIONS

Adams, et al. Document No. 48:46246, retrieved from STN; Journal of Organic Chemistry (1953); entered in STN on Apr. 22, 2001.*
Vivona, et al. Document No. 84:104794, retrieved from STN; Journal of Heterocyclic Chemistry (1975): entered in STN on May 12, 1984.*
Burow, et al. Document No. 101:171235, retrieved from STN; entered in STN on Nov. 10, 1984.*
Buscemi, et al. Document No. 112:55755, retrieved from STN; Heterocycles (1989); entered in on STN on Feb. 17, 1990.*
Unangst, et al. Document No. 117:191765, retrieved from STN; Journal of Medicinal Chemistry (1992); entered in STN Nov. 15, 1992.*
Buscemi, et al. Document No. 123:285007, retrieved from STN; Tetrahedron (1995); entered in STN on May 16, 1995.*
Breinlinger, et al. Document No. 150:168325, retrieved from STN; entered in STN on Jan. 23, 2009.*
Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*
J.T. Mendell, H.C. Diez, "When the message goes awry: disease-producing mutations that influence mRNA content and performance", Cell 107 (2001) 411-414.
L. Bidou, V. Allamand, J.P. Rousset, O. Namy, "Sense from nonsense: therapies for premature stop codon diseases", Trends Mol. Med. 18 (2012) 679-688.
T. Goldmann, N. Overlack, F. Moller, V. Belakhov, M. van Wyk, T. Baasov, U. Wolfrum, K. Nagel-Wolfrum,"A comparative evaluation of NB30, NB54 and PTC124 in translational read-through efficacy for treatment of an USH1C nonsense mutation", EMBO Mol. Med. 4 (2012) 1186-1199.
Sermet-Gaudelus I, Boeck KD, Casimir GJ, Vermeulen F, Leal T, Mogenet A, Roussel D, Fritsch J, Hanssens L, Hirawat S, Miller NL, Constantine S, Reha A, Ajayi T, Elfring GL, Miller LL. Ataluren "(PTC124) induces cystic fibrosis transmembrane conductance regulator protein expression and activity in children with nonsense mutation cystic fibrosis.", Am J Respir Crit Care Med. Nov. 15, 2010;182(10):1262-72.
S.M. Rowe, J.P. Clancy, "Pharmaceuticals targeting nonsense mutations in genetic diseases", Biodrugs 23 (2009) 165-174.
L.S. Mc Coy, Y. Xie, Y. Tor, "Antibiotics that target protein synthesis", Wiley Interdiscip. Rev. RNA 2 (2011) 209-232.

(Continued)

*Primary Examiner* — Shawquia Jackson
(74) *Attorney, Agent, or Firm* — Volpe Koenig

(57) ABSTRACT

Are disclosed oxadiazole derivatives, their use as medicaments and in particular for the treatment of diseases associated with the presence of a nonsense mutation in the gene or a premature stop codon in the mRNA, pharmaceutical formulation comprising said oxadiazole derivatives and prodrug or mixture thereof and the methods for the preparation of said Oxadiazole derivatives.

8 Claims, 7 Drawing Sheets

Specification includes a Sequence Listing.

(56) References Cited

OTHER PUBLICATIONS

V. Malik, L.R. Rodino-Klapac, L. Viollet, J R. Mendell, "Aminoglycoside-induced mutation suppression (stop codon readthrough) as a therapeutic strategy for Duchenne muscular dystrophy", Ther. Adv. Neurol. Disord. 3 (2010) 379-389.

J. Karijolich, Y.T. Yu, "Therapeutic suppression of premature termination codons: mechanisms and clinical considerations" (Review), Int. J. Mol. Med. 34 (2014) 355-362.

A. Prayle, A.R. Smyth, "Aminoglycoside use in cystic fibrosis: therapeutic strategies and toxicity", Curr. Opin. Pulm. Med. 16 (2010) 604-610.

E.M. Welch, et al. "PTC124 targets genetic disorders caused by nonsense mutations", Nature 447 (2007) 87-91.

Kerem E, Hirawat S, Armoni S, Yaakov Y, Shoseyov D, Cohen M, Nissim-Rafinia M, Blau H, Rivlin J, Aviram M, Elfring GL, Northcutt VJ, Miller LL, Kerem B, Wilschanski M., "Effectiveness of PTC124 treatment of cystic fibrosis caused by nonsense mutations: a prospective phase II trial.", Lancet. Aug. 30, 2008;372(9640):719-27.

Harmer, S. C.; Mohal, J. S.; Kemp, D.; Tinker, A., "Readthrough of long-QT syndrome type 1 nonsense mutations rescues function but alters the biophysical properties of the channel" Biochem J 2012, 443 (3), 635-42.

McElroy, S. P.; Nomura, T.; Torrie, L. S.; Warbrick, E.; Gartner,U.; Wood, G.; McLean, W. H., "A lack of premature termination codon read-through efficacy of PTC124 (Ataluren) in a diverse array of reporter assays." PLoS Biol 2013, 11 (6), e1001593.

Goldmann, T.; Overlack, N.; Moller, F.; Belakhov, V.; van Wyk, M.; Baasov, T.; Wolfrum, U.; Nagel-Wolfrum, K., "A comparative evaluation of NB30, NB54 and PTC124 in translational readthrough efficacy for treatment of an USH1C nonsense mutation." EMBO Mol Med 2012, 4 (11), 1186-99.

Sarkar, C.; Zhang, Z.; Mukherjee, A. B., "Stop codon read-through with PTC124 induces palmitoyl-protein thioesterase-1 activity, reduces thioester load and suppresses apoptosis in cultured cells from INCL patients." Mol Genet Metab 2011, 104 (3), 338-45.

L. Lentini, R. Melfi, A. Di Leonardo, A. Spinello, G. Barone, A. Pace, A. Palumbo Piccionello, I. Pibiri, "Towards a rationale for the PTC124 (Ataluren) promoted read-through of premature stop codons: a computational approach and GFP reporter cell-based assay," Mol. Pharm. 11 (2014) 653-664.

I. Pibiri, L. Lentini, R. Melfi, G. Gallucci, A. Pace, A. Spinello, G. Barone, A. Di Leonardo, "Enhancement of premature stop codon readthrough in the CFTR gene by Ataluren (PTC124) derivatives," Eur. J. Med. Chem. 101 (2015) 236-244.

Pibiri I., Lentini L., Tutone M., Melfi R., Pace A., Di Leonardo A. "Exploring the readthrough of nonsense mutations by non-acidic Ataluren analogues selected by ligand-based virtual screening," Eur. J. Med. Chem. 122 (2016) 429-435.

Senger J. et al., 2015, J. Med. Chem, "Synthesys and Biological Investigation of Oxazole Hydroxamates as Highly Selective Histone Deacetylase 6 (HDAC6) Inhibitors", 59(4), 1545-1555.

* cited by examiner

OXADIAZOLE DERIVATIVES FOR THE TREATMENT OF GENETIC DISEASES DUE TO NONSENSE MUTATIONS

BACKGROUND OF THE INVENTION

The present invention refers to the pharmaceutical field since it relates to new oxadiazole derivatives for the treatment of diseases associated with the presence of a nonsense mutation in the gene or a premature stop codon in the mRNA.

STATE OF THE ART

Several cases of Mendelian genetic diseases are due to the presence of nonsense mutations in the DNA generating premature PTCs in the mRNA, able to interrupt the activity of a gene, making the product protein absent or not functional. This serious lack of functional protein is reflected in the establishment of a pathological condition in life Diseases such as Cystic Fibrosis (CF) and Duchenne Muscular Dystrophy (DMD), for the percentage related to nonsense mutations (J. T. Mendell, H. C. Diez, When the message goes awry: disease-producing mutations that influence mRNA content and performance, Cell 107 (2001) 411-414; L. Bidou, V. Allamand, J. P. Rousset, O. Namy, Sense from nonsense: therapies for premature stop codon diseases, Trends Mol. Med. 18 (2012) 679-688; T. Goldmann, N. Overlack, F. Moller, V. Belakhov, M. van Wyk, T. Baasov, U. Wolfrum, K. Nagel-Wolfrum, A comparative evaluation of NB30, NB54 and PTC124 in translational read-through efficacy for treatment of an USH1C nonsense mutation, EMBO Mol. Med. 4 (2012) 1186-1199).

The presence of nonsense mutations in the DNA generate premature termination codons (PTCs) in the mRNA, this class mutations interrupt the activity of a gene, making the product protein absent or not functional. Different types of nonsense mutations were observed in CF and are responsible for about 10% of cystic fibrosis (CF) cases worldwide; patients with CF lack adequate levels of the regulator CFTR, a chloride channel that is necessary for normal function of vital organs such as the lung, pancreas, liver (Sermet-Gaudelus I, Boeck K D, Casimir G J, Vermeulen F, Leal T, Mogenet A, Roussel D, Fritsch J, Hanssens L, Hirawat S, Miller N L, Constantine S, Reha A, Ajayi T, Elfring G L, Miller L L. Ataluren (PTC124) induces cystic fibrosis transmembrane conductance regulator protein expression and activity in children with nonsense mutation cystic fibrosis, Am J Respir Crit Care Med. 2010 Nov. 15; 182(10):1262-72).

A potential treatment of this genetic alteration is to promote the readthrough of PTCs by the use of drugs with readthrough action (TRIDs)(S. M. Rowe, J. P. Clancy, Pharmaceuticals targeting nonsense mutations in genetic diseases, Biodrugs 23 (2009) 165-174)

Aminoglycosides antibiotics, such as gentamicin, tobramycin, amikacin, were considered as potential treatment for conditions caused by nonsense mutations, to suppress the normal proofreading function of the ribosome, leading to insertion of a near-cognate amino acid at a PTC and translation of full-length protein (L. S. Mc Coy, Y. Xie, Y. Tor, Antibiotics that target protein synthesis, Wiley Interdiscip. Rev. RNA 2 (2011) 209-232; V. Malik, L. R. Rodino-Klapac, L. Viollet, J. R. Mendell, Aminoglycoside-induced mutation suppression (stop codon read-through) as a therapeutic strategy for Duchenne muscular dystrophy, Ther. Adv. Neurol. Disord. 3 (2010) 379-389; J. Karijolich, Y. T. Yu, Therapeutic suppression of premature termination codons: mechanisms and clinical considerations (Review), Int. J. Mol. Med. 34 (2014) 355-362).

Unfortunately, aminoglycoside action lacks specificity resulting in readthrough of many correctly positioned stop codons. Moreover, a complication of long-term use of aminoglycosides is their nephrotoxicity and ototoxicity (A. Prayle, A. R. Smyth, Aminoglycoside use in cystic fibrosis: therapeutic strategies and toxicity, Curr. Opin. Pulm. Med. 16 (2010) 604-610).

At now, the lead product candidate for the treatment of patients with genetic disorders that arise from a nonsense mutation is Ataluren, a small molecule, that is used at lower dose with respect to aminoglycosides, inducing the readthrough of premature but not normal termination codons without the toxicity of aminoglycosides (E. M. Welch, E. R. Barton, J. Zhuo, Y. Tomizawa, W. J. Friesen, P. Trifillis, S. Paushkin, M. Patel, C. R. Trotta, S. Hwang, R. G. Wilde, G. Karp, J. Takasugi, G. Chen, S. Jones, H. Ren, Y. C. Moon, D. Corson, A. A. Turpoff, J. A. Campbell, M. M. Conn, A. Khan, N. G. Almstead, J. Hedrick, A. Mollin, N. Risher, M. Weetall, S. Yeh, A. A. Branstrom, J. M. Colacino, J. Babiak, W. D. Ju, S. Hirawat, V. J. Northcutt, L. L. Miller, P. Spatrick, F. He, M. Kawana, H. Feng, A. Jacobson, S. W. Peltz, H. L. Sweeney, PTC124 targets genetic disorders caused by nonsense mutations, Nature 447 (2007) 87-91; Kerem E, Hirawat S, Armoni S, Yaakov Y, Shoseyov D, Cohen M, Nissim-Rafinia M, Blau H, Rivlin J, Aviram M, Elfring G L, Northcutt V J, Miller L L, Kerem B, Wilschanski M., Effectiveness of PTC124 treatment of cystic fibrosis caused by nonsense mutations: a prospective phase II trial, Lancet. 2008 Aug. 30; 372(9640):719-27; Sermet-Gaudelus I, Boeck K D, Casimir G J, Vermeulen F, Leal T, Mogenet A, Roussel D, Fritsch J, Hanssens L, Hirawat S, Miller N L, Constantine S, Reha A, Ajayi T, Elfring G L, Miller L L. Ataluren (PTC124) induces cystic fibrosis transmembrane conductance regulator protein expression and activity in children with nonsense mutation cystic fibrosis, Am J RespirCrit Care Med. 2010 Nov. 15; 182(10):1262-72).

Ataluren has a controversial preclinic and clinic history as some studies did not find evidence of its readthrough activity (Harmer, S. C.; Mohal, J. S.; Kemp, D.; Tinker, A., Readthrough of long-QT syndrome type 1 nonsense mutations rescues function but alters the biophysical properties of the channel. Biochem J 2012, 443 (3), 635-42; McElroy, S. P.; Nomura, T.; Torrie, L. S.; Warbrick, E.; Gartner, U.; Wood, G.; McLean, W. H., A lack of premature termination codon read-through efficacy of PTC124 (Ataluren) in a diverse array of reporter assays. PLoS Biol 2013, 11 (6), e1001593).

Other studies indicated an effective readthrough activity (Goldmann, T.; Overlack, N.; Moller, F.; Belakhov, V.; van Wyk, M.; Baasov, T.; Wolfrum, U.; Nagel-Wolfrum, K., A comparative evaluation of NB30, NB54 and PTC124 in translational read-through efficacy for treatment of an USH1C nonsense mutation. EMBO Mol Med 2012, 4 (11), 1186-99; Sarkar, C.; Zhang, Z.; Mukherjee, A. B., Stop codon read-through with PTC124 induces palmitoyl-protein thioesterase-1 activity, reduces thioester load and suppresses apoptosis in cultured cells from INCL patients. Mol Genet Metab 2011, 104 (3), 338-45).

Ataluren has passed Phase III clinical trials for DMD patients and is currently licensed in the European Economic Area for the treatment of nonsense mutation Duchenne muscular dystrophy (nmDMD) in ambulatory patients aged five years and older under the trade name Translarna™ (6 Mar. 2017 PTC Therapeutics, Release Agency). Currently Ataluren is the first oral therapy to intervene on the molecular mechanisms involved in gene reading and translation into proteins. On the contrary, Phase III clinical trials for CF patients has been suspended because the results, unless positive, were considered not statistically significant. Recently, PTC Therapeutics closed ongoing extension studies and withdraw the application at FDA for marketing authorization in cystic fibrosis. (2 Mar. 2017 PTC Therapeutics, Release Agency).

The same inventors of the present invention, suggested that it may be an interaction between the mRNA containing the UGA nonsense mutation and Ataluren as a mechanism of readthrough (L. Lentini, R. Melfi, A. Di Leonardo, A. Spinello, G. Barone, A. Pace, A. Palumbo Piccionello, I. Pibiri, Towards a rationale for the PTC124 (Ataluren) promoted read-through of premature stop codons: a computational approach and GFP reporter cell-based assay, Mol. Pharm. 11 (2014) 653-664; I. Pibiri, L. Lentini, R. Melfi, G. Gallucci, A. Pace, A. Spinello, G. Barone, A. Di Leonardo, Enhancement of premature stop codon readthrough in the CFTR gene by Ataluren (PTC124) derivatives, Eur. J. Med. Chem. 101 (2015) 236-244).

Therefore, the same inventors of the present invention, in the attempt to shed light on these controversial results as well to get a better knowledge of the mechanism of action of small molecules as Ataluren, already designed and synthesized analogues of Ataluren to be tested in human cultured cells (I. Pibiri, L. Lentini, R. Melfi, G. Gallucci, A. Pace, A. Spinello, G. Barone, A. Di Leonardo, Enhancement of premature stop codon readthrough in the CFTR gene by Ataluren (PTC124) derivatives, Eur. J. Med. Chem. 101 (2015) 236-244; Pibiri I., Lentini L., Tutone M., Melfi R., Pace A., Di Leonardo A. Exploring the readthrough of nonsense mutations by non-acidic Ataluren analogues selected by ligand-based virtual screening, Eur. J. Med. Chem. 122 (2016) 429-435).

International patent applications WO2006044682, WO2006044505, WO2006044503, WO2006044502 and WO2006044456 discloses heterocyclic compounds for treating diseases associated with nonsense mutations in a mRNA and more in particular, International patent application WO2006/044456 discloses 1,2,4,-oxadiazole derivatives for the treatment of nonsense mutations.

International patent applications WO2006110483 and WO2008045566 disclose Ataluren for treating diseases associated with nonsense mutations.

International patent application WO2008130370 discloses 1,2,4, oxadiazoles benzoic acid compounds for the modulation of premature translation or nonsense mRNA decay.

International patent application WO2011072281 discloses 1,2,4, oxadiazoles benzoic acid compounds for treating methylmalonic acidemia.

International patent application WO2015134711 discloses 1,2,4, oxadiazoles benzoic acid compounds for the treatment of diseases associated with nonsense mutation or premature codon stop.

International patent application WO2015188037 discloses 1,2,4, oxadiazoles benzoic acid compounds for the treatment of mucopolysaccharidosis.

US patent application publication US2017/0204073 discloses compounds for nonsense suppression, and methods for their use.

International patent application WO2014/085490 and publication Senger J. et al., 2015, J. Med. Chem, "Synthesys and Biological Investigation of Oxazole Hydroxamates as Highly Selective Histone Deacetylase 6 (HDAC6) Inhibitors", 59(4), 1545-1555 disclose the preparation of 5-phenyl-1,2,4-oxadiazole-3-carboxylate by a two step synthesis wherein an open intermediate is first formed in DCM, isolated and then cyclized by heating in the presence of a base.

Technical Problem

The compound known in the art, used to readthrough premature termination codons (PTCs) caused by nonsense mutations, present several drawbacks.

As previously discussed, aminoglycosides known in the art present several drawbacks: lack of specificity and may readthrough not-mutated stop codons; in long-term treatment cause nephrotoxicity and ototoxicity; known experimental results on ataluren cytotoxicity are conflicting, ataluren has low bioavailability and when it restores readthrough of mutated stop codons the protein production is lower than in wild types.

It is self evident that there is a long felt need for new readthrough promoters which can be efficiently used for the treatment of genetic diseases caused by mutations in stop codons.

The inventors of the present invention, in view of the findings of the prior art, investigated on molecules able to act on the genetic defect that disrupts the normal course of protein production, by the gene with a nonsense mutation, and unexpectedly synthesized and characterized a new class of compounds able to readthrough premature termination codons which can be used for the treatment of diseases caused by nonsense mutations.

OBJECT OF THE INVENTION

Therefore, with reference to the attached claims and the following detailed description, the above technical problem is solved by the compound 2,3,4,5,6-pentafluoro-N-(5-(perfluorophenyl)-1,2,4-oxadiazol-3-yl)benzamide, its method of preparation, its use as a medicament, its use for the treatment of diseases caused by nonsense mutation and pharmaceutical composition comprising a pharmacologically effective amount of 2,3,4,5,6-pentafluoro-N-(5-(perfluorophenyl)-1,2,4-oxadiazol-3-yl)benzamide or its prodrug and pharmaceutically acceptable excipients.

Compound N-(5-methyl-1,2,4-oxadiazol-3-yl)acetamide for use as a medicament and for use in the treatment of diseases caused by nonsense mutation and pharmaceutical composition comprising a pharmacologically effective amount of N-(5-methyl-1,2,4-oxadiazol-3-yl)acetamide or its prodrug and pharmaceutically acceptable excipients.

Compounds of formula (I)

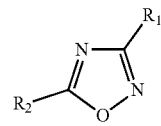

Wherein
R1 is selected from the group consisting of: amide derivatives, ester derivatives
R2 is selected from the group consisting of: alkyl, aryl, perfluoroalkyl, polyfluoroaryl.
for use in the treatment of diseases caused by nonsense mutations and pharmaceutical composition comprising a pharmacologically effective amount of at least one compound of formula (I) or its prodrug or mixture thereof and pharmaceutically acceptable excipients, for use in the treatment of diseases caused by UGA nonsense mutations.

DETAILED DESCRIPTION OF THE INVENTION

Definitions

Figure 1:
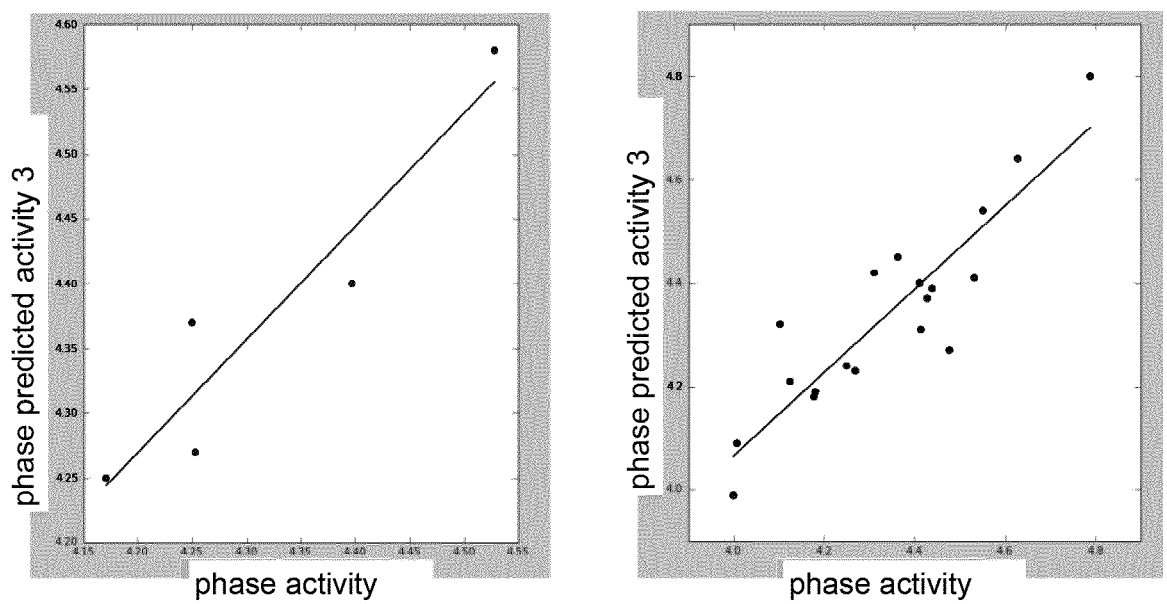
FIG. 1 shows in the left panel the test-set and in the right panel the training-set plots for Hypo.7.

Within the meaning of the present invention diseases caused by nonsense mutations means disease caused by a point mutation in the sequence of DNA resulting in a premature stop codon in the transcribed mRNA, and in a truncated, incomplete, and non-functional protein product, wherein stop codons in RNA are UAG (amber), UAA (ochre) and UGA (opal). Nonsense mutation generates UGA, UAA and UAG premature termination codons.

The diseases caused by nonsense mutations can be CNS diseases, inflammatory diseases, neurodegenerative diseases, autoimmune diseases, cardiovascular diseases, pulmonary diseases. More specifically are cancer or other proliferative diseases, amyloidosis, Alzheimer's disease, atherosclerosis, giantism, dwarfism, hypothyroidism, hyperthyroidism, cystic fibrosis, aging, obesity, Parkinson's disease, Niemann Pick's disease, familial hypercholesterolemia, retinitis pigmentosa, Marfan syndrome, lysosomal storage disorders, muscular dystrophies, cystic fibrosis, hemophilia, or classical late infantile neuronal ceroid lipofuscinosis (LINCL), Cystic Fibrosis (CF), Duchenne Muscular Dystrophy (DMD), atherosclerosis, Alzheimer's disease, amyloidosis, retinitis pigmentosa, Usher's syndrome, ALS, multiple sclerosis.

Within the meaning of the present invention pro-drug means a compound that, after administration, is metabolized into a pharmacologically active compound.

Within the meaning of the present invention pharmaceutically acceptable excipients means any chemical alongside the active ingredient of a medication, such as, and not limited to, long-term stabilization agents, bulking agents, fillers, diluents, agents facilitating drug absorption, agents reducing viscosity, agents enhancing solubility, agents facilitating powder flowability or non-stick properties, agents aiding in vitro stability, agents preventing denaturation or aggregation, agents improving shelf life, depending also upon the route of administration and the dosage form, which can be selected by the person skilled in the art in view of his common general knowledge.

Object of the invention is 2,3,4,5,6-pentafluoro-N-(5-(perfluorophenyl)-1,2,4-oxadiazol-3-yl)benzamide.

An other object of the present invention is the method of preparation of 2,3,4,5,6-pentafluoro-N-(5-(perfluorophenyl)-1,2,4-oxadiazol-3-yl)benzamide by acylation with perfluorobenzoyl chloride of amine 2 according to the following reaction

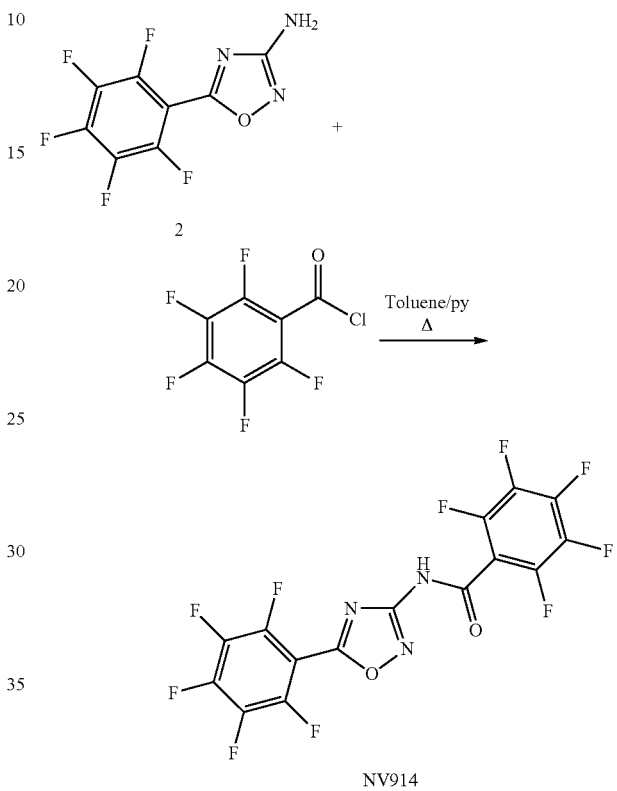

wherein an equal amount of perfluorobenzoyl chloride and pyridine are added to the amine dissolved in toluene, until consumption of starting material, followed by removal of the solvent and addition of water to the residue, then the final product is obtained by further purification.

Preferably purification is performed by extraction with ethyl acetate and chromatographic separation on silica gel using mixtures of petroleum ether and ethyl acetate as eluent followed by crystallization.

An other object of the present invention is 2,3,4,5,6-pentafluoro-N-(5-(perfluorophenyl)-1,2,4-oxadiazol-3-yl)benzamide for use as a medicament.

An other object of the present invention is 2,3,4,5,6-pentafluoro-N-(5-(perfluorophenyl)-1,2,4-oxadiazol-3-yl)benzamide for use for the treatment of diseases caused by nonsense mutations.

An other object of the present invention is a pharmaceutical composition comprising a pharmacologically effective amount of 2,3,4,5,6-pentafluoro-N-(5-(perfluorophenyl)-1,2,4-oxadiazol-3-yl)benzamide or its prodrug and pharmaceutically acceptable excipients.

An other object of the present invention is N-(5-methyl-1,2,4-oxadiazol-3-yl)acetamide for use as a medicament.

An other object of the present invention is N-(5-methyl-1,2,4-oxadiazol-3-yl)acetamide for use in the treatment of diseases caused by nonsense mutation.

An other object of the present invention is a pharmaceutical composition comprising a pharmacologically effective amount of N-(5-methyl-1,2,4-oxadiazol-3-yl)acetamide or its prodrug and pharmaceutically acceptable excipients.

An other object of the present invention is compound of formula (I)

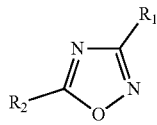

Wherein
R1 is selected from the group consisting of: amide derivatives, ester derivatives
R2 is selected from the group consisting of: alkyl, perfluoroalkyl, aryl, polyfluoroaryl
for use in the treatment of diseases caused by nonsense mutations.

Preferably when R1 is amide derivative is selected from the group consisting of: alkyl amide, aryl amide, polyfluoroaryl amide. Preferably when R1 is ester derivative is polyfluoroaryl ester.

More preferably R1 is selected from the group consisting of:

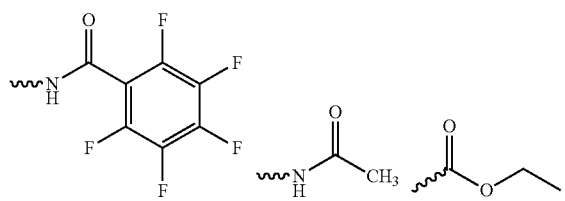

Preferably when R2 is alkyl is selected from the group consisting of: methyl, ethyl, propyl.

Preferably when R2 is perfluoroalkyl is selected from the group consisting of: perfluoromethyl, perfluoropropyl, perfluoroheptyl.

Preferably when R2 is aryl is phenyl.

More preferably R2 is selected from the group consisting of:

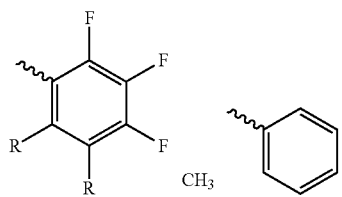

for use in the treatment of diseases caused by nonsense mutations and pharmaceutical.

More preferably compounds of formula (I) are selected from the group consisting of:
2,3,4,5,6-pentafluoro-N-(5-(perfluorophenyl)-1,2,4-oxadiazol-3-yl)benzamide
N-(5-methyl-1,2,4-oxadiazol-3-yl)acetamide
ethyl 5-phenyl-1,2,4-oxadiazole-3-carboxylate An other object of the present invention are composition comprising a pharmacologically effective amount of at least one compound of formula (I) or its prodrug or mixture thereof and pharmaceutically acceptable excipients, for use in the treatment of diseases caused by nonsense mutations.

Another object of the present invention is the method of preparation of ethyl 5-phenyl-1,2,4-oxadiazole-3-carboxylate by amidoxime route according to the following reaction

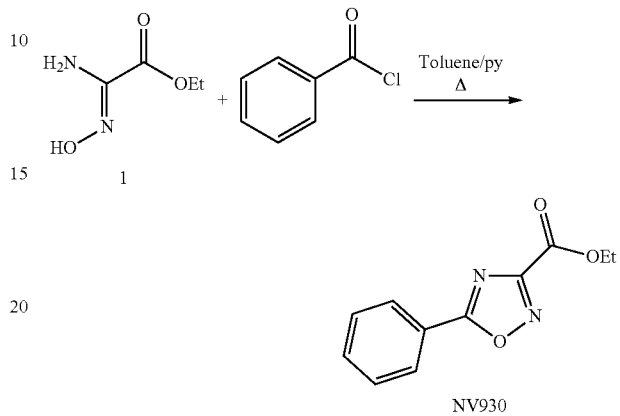

Wherein amidoxime 1 was dissolved in toluene, then equal amount of aroyl chloride and pyridine were added until consumption of starting material, followed by removal of the solvent and addition of water to the residue, then the final product is obtained by further purification.

Preferably purification is performed by extraction with ethyl acetate and chromatographic separation on silica gel using mixtures of petroleum ether and ethyl acetate as eluent allowed to obtain the desired oxadiazole and further purification by crystallization.

Preferably the disease caused by nonsense mutations is selected from the group consisting of: CNS diseases, inflammatory diseases, neurodegenerative diseases, autoimmune diseases, cardiovascular diseases, pulmonary diseases, proliferative diseases.

More preferably the disease caused by nonsense mutations is selected from the group consisting of cancer, amyloidosis, Alzheimer's disease, atherosclerosis, giantism, dwarfism, hypothyroidism, hyperthyroidism, cystic fibrosis, aging, obesity, Parkinson's disease, Niemann Pick's disease, familial hypercholesterolemia, retinitis pigmentosa, Marfan syndrome, lysosomal storage disorders, muscular dystrophies, cystic fibrosis, hemophilia, or classical late infantile neuronal ceroid lipofuscinosis (LINCL), Cystic Fibrosis (CF), Duchenne Muscular Dystrophy (DMD), atherosclerosis, Alzheimer's disease, amyloidosis, retinitis pigmentosa, Usher's syndrome, ALS, multiple sclerosis.

Even more preferably the disease caused by UGA nonsense mutations is Cystic Fibrosis (CF), Duchenne Muscular Dystrophy (DMD).

EXAMPLES 58 molecules have been synthetized, some of them identified by a virtual screening, and evaluate their activity by using different assays: the F-Luc assay using a vector containing a UGA in the cDNA of the F-Luc and epithelial rat cells transfected with a CFTR nonsense mutated cDNA.

The tests were focused in particular on CFTR as a model, due to the lack of therapy and the wide diffusion of this genetic disease.

Example 1 Virtual Design and Synthesis

Concerning the 3D-QSAR pharmacophore modelling, used processing procedures for the structures and models generation were as disclosed in [Almerico, A. M., Tutone, M., Lauria, A. 3D-QSAR pharmacophore modeling and in silico screening of new Bcl-xl inhibitors (2010) European Journal of Medicinal Chemistry, 45 (11), pp. 4774-4782; Lauria, A., Ippolito, M., Fazzari, M., Tutone, M., Di Blasi, F., Mingoia, F., Almerico, A. M. IKK-β inhibitors: An analysis of drug-receptor interaction by using Molecular Docking and Pharmacophore 3D-QSAR approaches (2010) Journal of Molecular Graphics and Modelling, 29 (1), pp. 72-81; Almerico, A. M., Tutone, M., Lauria, A. Receptor-guided 3D-QSAR approach for the discovery of c-kit tyrosine kinase inhibitors (2012) Journal of Molecular Modeling, 18 (7), pp. 2885-2895; Almerico, A. M., Tutone, M., Pantano, L., Lauria, A. A3 adenosine receptor: Homology modeling and 3D-QSAR studies (2013) Journal of Molecular Graphics and Modelling, 42, pp. 60-72; Perricone, U., Wieder, M., Seidel, T., Langer, T., Padova, A., Almerico, A. M., Tutone, M. A Molecular Dynamics-Shared Pharmacophore Approach to Boost Early-Enrichment Virtual Screening: A Case Study on Peroxisome Proliferator-Activated Receptorα(2017) ChemMedChem, 2017, 12, 1399-1407; Pibiri, I., Lentini, L., Tutone, M., Melfi, R., Pace, A., Di Leonardo, A. Exploring the readthrough of nonsense mutations by non-acidic Ataluren analogues selected by ligand-based virtual screening (2016) European Journal of Medicinal Chemistry, 122, pp. 429-435; Tutone, M., Pantano, L., Lauria, A., Almerico, A. M. Molecular dynamics, dynamic site mapping, and highthroughput virtual screening on leptin and the Ob receptor as anti-obesity target (2014) Journal of Molecular Modeling, 20 (5), Phase, version 4.3, Schrödinger, LLC, New York, N.Y., 2015. Dixon, S. L.; Smondyrev, A. M.; Knoll, E. H.; Rao, S. N.; Shaw, D. E.; Friesner, R. A., "PHASE: A New Engine for Pharmacophore Perception, 3D QSAR Model Development, and 3D Database Screening. 1. Methodology and Preliminary Results," J. Comput. Aided Mol. Des., 2006, 20, 647-671. and Phase software was Phase, version 4.3, Schrödinger, LLC, New York, N.Y., 2015.

Models generated were measured according appropriate measures of goodness-of-fit, robustness, and predictive capability.

Used statistics for goodness-of fit are: R2, SD (standard deviation), F (Fisher test), p value, RMSE (rootmean square error), Pearson-R. Used statistics to measure robustness of the model are: Q2(eq.1).

$$q^2 = 1 - \frac{\sum_{i=1}^{training}(y_i - \hat{y}_i)^2}{\sum_{i=1}^{training}(y_i - \bar{y})^2} \qquad \text{Eq. 1}$$

Where $y_i, \hat{y}_i$ are the actual and predicted activities of the ith molecule, respectively, and $\bar{y}$ is the average activity of all molecules.

Predictive capability of the models generated was assessed by means of the external validation of the test set. Used statistics for external validation are: Q2ext (eq.2), Golbraikh and Tropsha parameters R20 e R'20, and k and k'[29], r2m metrics >0.65, $$q^2_{ext} = 1 - \frac{\sum_{i=1}^{test}(y_i - \hat{y}_i)^2}{\sum_{i=1}^{test}(y_i - \bar{y})^2} \qquad \text{Eq. 2}$$

Where $y_i, \hat{y}_i$ are the actual and predicted activities of the ith molecule, respectively, $\bar{y}_{tr}$ is the average activity of all molecules in the training set.

All solvents and reagents were commercially available. All synthesized compounds were purified by chromatography and analysed by IR, HRMS, GC-MS, and NMR. Purity of synthesized compounds was verified prior to biological tests by chromatographic analyses and NMR (see supplementary material) and in all the cases purity was higher than 95%. IR spectra have been registered with a Shimadzu FTIR-8300 spectrophotometer; melting points have been determined on a Reichart-Thermovar hotstage Kofler and are uncorrected. NMR spectra have been registered on a Bruker AVANCE DMX 300 using CDCl3 and DMSO as solvent. HRMS spectra were recorded by analysing a 50 ppm solution of the compound in a 6540 UHD Accurate-Mass Q-TOF LC/MS (Agilent Technologies) equipped with a Dual AJS ESI source. GC-MS spectra have been registered by using either an Agilent 7890B/7000C GC-MS-TQ or a GC-MS Shimadzu QP-2010 Instrument. Flash chromatography was performed by using silica gel (Merck, 0.040-0.063 mm) and mixtures of ethyl acetate and petroleum ether (fraction boiling in the range of 40-60° C.) in various ratios.

The QikProp program (QikProp, version 4.4, Schrödinger, LLC, New York, N.Y., 2015) was used to obtain the ADME properties of our compounds, and ATALUREN. It predicts both physically significant descriptors and pharmaceutically relevant features, such as principal descriptors and physiochemical properties. It also evaluated the drug-like acceptability of the compounds, based on Lipinski's rule of five, essential for rational drug design.

Molecular Design of the new molecules has been realized by a High Throughput Virtual Screening (HTVS) of an in-house library of about 30000 molecules (I. Pibiri, L. Lentini, R. Melfi, G. Gallucci, A. Pace, A. Spinello, G. Barone, A. Di Leonardo, Enhancement of premature stop codon readthrough in the CFTR gene by Ataluren (PTC124) derivatives, Eur. J. Med. Chem. 101 (2015) 236-244; Pibiri I., Lentini L., Tutone M., Melfi R., Pace A., Di Leonardo A. Exploring the readthrough of nonsense mutations by non-acidic Ataluren analogues selected by ligand-based virtual screening, Eur. J. Med. Chem. 122 (2016) 429-435).

The results disclosed in (Pibiri I., Lentini L., Tutone M., Melfi R., Pace A., Di Leonardo A. Exploring the readthrough of nonsense mutations by non-acidic Ataluren analogues selected by ligand-based virtual screening. Eur. J. Med. Chem. 122 (2016) 429-435) have been refined with 3D-QSAR (quantitative structure-activity relationships) pharmacophore modelling. The endpoint to build QSAR models was the luciferase activity known data. These values were converted to pFLUC (−log FLUC) values. In order to find the common pharmacophore hypothesis, we divided the 24 compounds in three different classes of activity related to the FLUC values (Pharm set). We considered as active, compounds with FLUC values >4.52 (ATALUREN FLUC value), as inactives, compounds with FLUC values ≤4.00, and as moderate actives, compounds with 4.39≤FLUC values ≤4,51. Dataset was randomly split into a training set (19 compounds) for models generation, and test set (5 compounds) for the validation of developed models, as reported in Table 1.

TABLE 1

| Compound | Chemical name | QSAR set | RLU values Exp. | RLU values Pred. | Pharm Set | Fitness |
|---|---|---|---|---|---|---|
| ATALUREN | 3-(5-(2-Fluorophenyl)-1,2,4-oxadiazol-3-yl)benzoic acid | Test | 4.528 | 4.58 | Active | 3.00 |
| 1-NV1103 [1] | Methyl 3-(5-(2-fluorophenyl)-1,2,4-oxadiazol-3-yl)benzoate) | Training | 4.532 | 4.41 | Active | 2.94 |
| 2-NV1127 [1] | Methyl 3-(5-(3-fluorophenyl)-1,2,4-oxadiazol-3-yl)benzoate) | Training | 4.477 | 4.27 | Moderate | 2.79 |
| 3-NV1133 [1] | 3-(5-(3-Fluorophenyl)-1,2,4-oxadiazol-3-yl)benzoic acid | Training | 4.628 | 4.64 | Active | 2.82 |
| 4-NV1128 [1] | Methyl 3-(5-(2,4,5-trifluorophenyl)-1,2,4-oxadiazol-3-yl)benzoate) | Test | 4.397 | 4.40 | Moderate | 2.87 |
| 5-NV1173 [1] | 3-(5-(2,4,5-Trifluorophenyl)-1,2,4-oxadiazol-3-yl)benzoic acid | Training | 4.788 | 4.80 | Active | 2.90 |
| 6-NV1153 [1] | Methyl 3-(5-(4-fluorophenyl)-1,2,4-oxadiazol-3-yl)benzoate) | Training | 4.125 | 4.21 | Inactive | 2.78 |
| 7-NV1149 [1] | Methyl 3-(5-(2,3-difluorophenyl)-1,2,4-oxadiazol-3-yl)benzoate) | Training | 4.103 | 4.32 | Inactive | 2.91 |
| 8-NV1170 [1] | Methyl 3-(5-(2,3-difluorophenyl)-1,2,4-oxadiazol-3-yl)ben zoate) | Training | 4.311 | 4.42 | Moderate | 2.91 |
| 9-NV1175 [1] | Methyl 3-(5-(3,4-difluorophenyl)-1,2,4-oxadiazol-3-yl)ben- zoate) | Training | 4.269 | 4.23 | Moderate | 2.76 |
| 10-NV1171 [1] | Methyl 3-(5-(2,4-difluorophenyl)-1,2,4-oxadiazol-3-yl)ben- zoate) | Training | 4.439 | 4.39 | Moderate | 2.90 |
| 11-NV1174 [1] | Methyl 3-(5-(2,6-difluorophenyl)-1,2,4-oxadiazol-3-yl)ben- zoate) | Training | 4.414 | 4.31 | Moderate | 2.80 |
| 12-NV1798 [1] | 3-Toluyl, 5-(2-fluorophenyl)-1,2,4-oxadiazole | Training | 4.178 | 4.18 | Inactive | 1.65 |
| 13-NV1951 [1] | Methyl 3-(5-(perfluorophenyl)-1,2,4-oxadiazol-3-yl)benzoate) | Training | 4.008 | 4.09 | Inactive | 2.71 |
| 14-NV1954 [1] | 3-(5-(Perfluorophenyl)-1,2,4-oxadiazol-3-yl)benzoic acid | Test | 4.171 | 4.25 | Inactive | 2.74 |
| 15-NV1859 [2] | 3-(2'-pyridyl)-5-(3'-cyanophenyl)-1,2,4-oxadiazole | Training | 4.363 | 4.25 | Moderate | 2.77 |
| 16-NV1861 [2] | 3-(4'-pyridyl)-5-(3'-toluyl)-1,2,4-oxadiazole | Training | 4.250 | 4.24 | Moderate | 2.76 |
| 17-NV1879 [2] | 3-(3'-pyridyl)-5-(3'-toluyl)-1,2,4-oxadiazole | Training | 4.411 | 4.40 | Moderate | 2.78 |
| 18-NV1883 [2] | 3-(3'-phenyl)-5-(3'-toluyl)-1,2,4-oxadiazole | Training | 4.428 | 4.37 | Moderate | 2.76 |
| 19-NV1894 [2] | 3-(3-toluyl), 5-(2-toluyl)-1,2,4-oxadiazole | Test | 4.250 | 4.37 | Moderate | 2.78 |
| 20-NV1905 [3] | 3-(3-toluyl), 5-(3-toluyl)-1,2,4-oxadiazole | Training | 4.181 | 4.19 | Inactive | 2.74 |

TABLE 1-continued

| Compound | Chemical name | QSAR set | RLU values Exp. | RLU values Pred. | Pharm Set | Fitness |
|---|---|---|---|---|---|---|
| 21-NV1898 [2] | 3-(2-pyridyl)-5-(3'-toluyl)-1,2,4-oxadiazole | Training | 4.551 | 4.54 | Active | 2.76 |
| 22-NV1919 [2] | 3-(4'-pyridyl)-5-(3'-anisoyl)-1,2,4-oxadiazole | Test | 4.253 | 4.27 | Moderate | 2.80 |
| 23-NV1940 [2] | 3-(2-pyridyl)-5-(3'-anisoyl)-1,2,4-oxadiazole | Training | 4.000 | 3.99 | Inactive | 1.66 |

In table 1 the compounds listed in the first column and labeled with the compounds named [1] are those disclosed in I. Pibiri, L. Lentini, M. Tutone, R. Melfi, A. Pace, A. Di Leonardo, "Exploring the readthrough of nonsense mutations by non-acidic Ataluren analogues selected by ligand-based virtual screening" Eur. J. Med. Chem., 2016, 122, 429-435.

In table 1 the compounds listed in the first column and labeled with the compounds named [2] are those disclosed in I. Pibiri, L. Lentini, R. Melfi, G. Gallucci, A. Pace, A. Spinello, G. Barone, A. Di Leonardo, "Enhancement of premature stop codon readthrough in the CFTR gene by Ataluren (PTC124) derivatives". Eur. J. Med. Chem., 2015, 101, 236-244.

In table 1 the compounds listed in the first column and labeled with the compounds named [3] are unpublished data.

Following Table 2 shows, wherein SD: standard deviation; F: Fisher test; P, significance level of variance ratio; RMSE: root mean square error.

TABLE 2

| ID | SD | $R^2$ | F | P | RMSE | Pearson-R |
|---|---|---|---|---|---|---|
| Hypo.7 | 0.1023 | 0.81 | 20.7 | 1.39E−02 | 0.0672 | 0.9482 |
| Hypo.8 | 0.104 | 0.80 | 19.8 | 1.76E−02 | 0.0941 | 0.9077 |

Following Table 3 shows the predictive capability values of models.

TABLE 3

| Hypo | $Q^2$ | $Q^2$ext | $R^2$ | $R^2_0$ | $R'^2_0$ | $R^2_m$ | $(R^2-R^2_0/R^2)$ | $(R^2-R'^2_0/R^2)$ | k | k' |
|---|---|---|---|---|---|---|---|---|---|---|
| Hypo.7 | 0.720 | 0.714 | 0.805 | 0.851 | 0.821 | 0.617 | −0.064 | −0.026 | 0.987 | 1.012 |
| Hypo.8 | 0.451 | 0.611 | 0.798 | 1.263 | 0.708 | 0.253 | −0.583 | 0.112 | 0.982 | 1.017 |

The models have been robustly validated, and Hypo.7 showed the best predictive capability, as showed in FIG. 1 and in Table 3.

Hypo.7 have been used as starting point to perform a new highthroughput virtual screening on an in-house database. From the top 5% of retrieved hits with the hypothesis, 58 Compounds have been prepared and tested.

The synthesis has been realized by optimized synthetic protocols and the reactions have been monitored by TLC (Thin Layer Chromatography). All the new synthesized compounds have been purified by column preparative chromatography performed with silica gel (Merck, 0.040-0.063 mm), by using mixtures of petroleum (fraction boiling in the range 40-60° C.) and Ethyl acetate as eluent.

Further purification was realized by crystallization. All the new synthesized compounds have been analysed by spectroscopic techniques such as 1H-NMR, 13C-NMR, UV, IR, GC-MS, to assess their molecular structure and their purity grade.

The synthesis and characterization of compounds NV914 2,3,4,5,6-pentafluoro-N-(5-(perfluorophenyl)-1,2,4-oxadiazol-3-yl)benzamide and NV930 ethyl 5-phenyl-1,2,4-oxadiazole-3-carboxylate is reported.

The synthesis and crystal structure of NV848 (3-acetylamino-5-methyl-1,2,4-oxadiazole) has been reported in the literature by some of the inventors of the present invention (N. Vivona, M. Ruccia, G. Cusmano, M. L. Marino, D. Spinelli, The thermally degenerate mononuclear rearrangement of 3-acetylamino-5-methyl-1,2,4-oxadiazole, J. Heterocycl. Chem. 1975, 12, 1327-1328; A. Mugnoli, G. Barone, S. Buscemi, C. Z. Lanza, A. Pace, M. Pani, D. Spinelli, On the structure of 3-acetylamino-5-methyl-1,2,4-oxadiazole and on the fully degenerate rearrangements (FDR) of its anion: a stimulating comparison between the results of in-silicon chemistry' and laboratory chemistry', Journal of Physical Organic Chemistry (2009), 22(11), 1086-1093; A. Pace, I. Pibiri, A. Palumbo Piccionello, S. Buscemi, N. Vivona, G. Barone, Experimental and DFT Studies on Competitive Heterocyclic Rearrangements. Part 2:1 A One-Atom Side-Chain versus the Classic Three-Atom Side-Chain (Boulton-Katritzky) Ring Rearrangement of 3-Acylamino-1,2,4-oxadiazoles, Journal of Organic Chemistry (2007), 72(20), 7656-7666.).

NV930, already reported in the literature, has been prepared by a different synthetic procedure: NV930 has been prepared by the classic amidoxime route: The amidoxime 1 (0.3 g) (prepared as reported in (P. S. Branco, S. Prabhakar, A. M. Lobo, D. J. Williams, "Reactions of hydroxylamines with ethyl cyanoformate. preparation of aminonitrones and their synthetic applications." tetrahedron 1992, 48, 6335-6360)) was dissolved in 50 mL of toluene in a 250 mL round bottomed flask. Then, 1.2 eq. of the appropriate aroyl chloride and 1.2 eq. of pyridine were added and the reaction mixture was refluxed for 6-8 h monitoring the reaction by TLC until consumption of starting material. The solvent was removed under vacuum and water was added to the residue. Extraction with ethyl acetate and chromatographic separation on silica gel using mixtures of petroleum ether and ethyl acetate as eluent allowed to obtain the desired oxadiazole, further purified by crystallization.

Reaction Yield 80%, MP 50-52° C., from Ethanol. 1H NMR (300 MHz, CDCl3) δ: 8.22 (d, J=7.2 Hz, 2H), 7.64 (t, J=7.4 Hz, 1H), 7.55 (t, J=7.4 Hz, 2H), 4.55 (q, J=7.1 Hz, 2H), 1.47 (t, J=7.1 Hz, 3H). FT-IR cm-1, 1720. HRMS for C11H10N2O3 found 219.0699 [M+H]+ (Calcd. 219.0691).

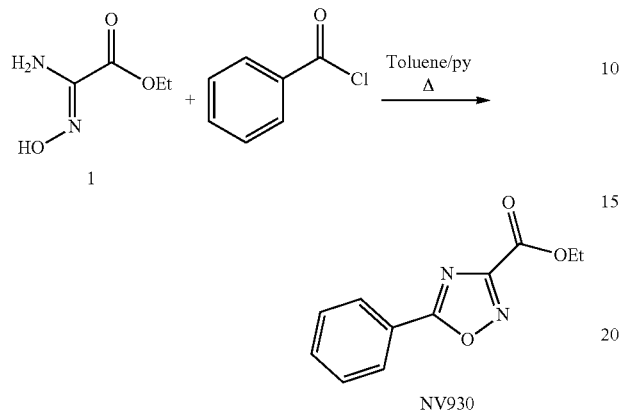

NV930

NV914 has been prepared by acylation with perfluorobenzoyl chloride of the amine 2, the latter reported in (Buscemi, Silvestre; Pace, Andrea; Pibiri, Ivana; Vivona, Nicolo; Caronna, Tullio, "Fluorinated heterocyclic compounds: an assay on the photochemistry of some fluorinated 1-oxa-2-azoles: an expedient route to fluorinated heterocycles" Journal of Fluorine Chemistry (2004), 125(2), 165-173, Buscemi, Silvestre; Pace, Andrea; Frenna, Vincenzo; Vivona, Nicolo "A generalized synthesis of 3-amino-5-aryl-, 3-amino-5-polyfluorophenyl-, and 3-amino-5-alkyl-1,2,4-oxadiazoles through ring-degenerate rearrangements" Heterocycles (2002), 57(5), 811-823; Buscemi, S.; Pace, A.; Calabrese, R.; Vivona, N.; Metrangolo, P." Fluorinated heterocyclic compounds. A photochemical synthesis of 3-amino-5-perfluoroaryl-1,2,4-oxadiazoles" Tetrahedron (2001), 57(27), 5865-5871).

1.2 eq. of perfluorobenzoyl chloride and 1.2 eq. of pyridine were added to the amine dissolved in toluene, and the reaction mixture was refluxed for 4 h monitoring the reaction by TLC until consumption of starting material. The solvent was removed under vacuum and water was added to the residue. Extraction with ethyl acetate and chromatographic separation on silica gel using mixtures of petroleum ether and ethyl acetate as eluent allowed to obtain the desired product, further purified by crystallization.

Reaction Yield 90%, MP 208-210° C., from Ethanol. 1H NMR (300 MHz, CDCl3) δ: 9.09 (s, 1H), FT-IR cm-1, 3290, 3180, 1750. HRMS for C15HF10N3O2 found 445.9917 [M+H]+ (Calcd. 445.9909).

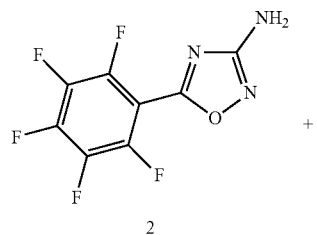

2

NV914

Example 2 In Vitro Tests

Figure 2:
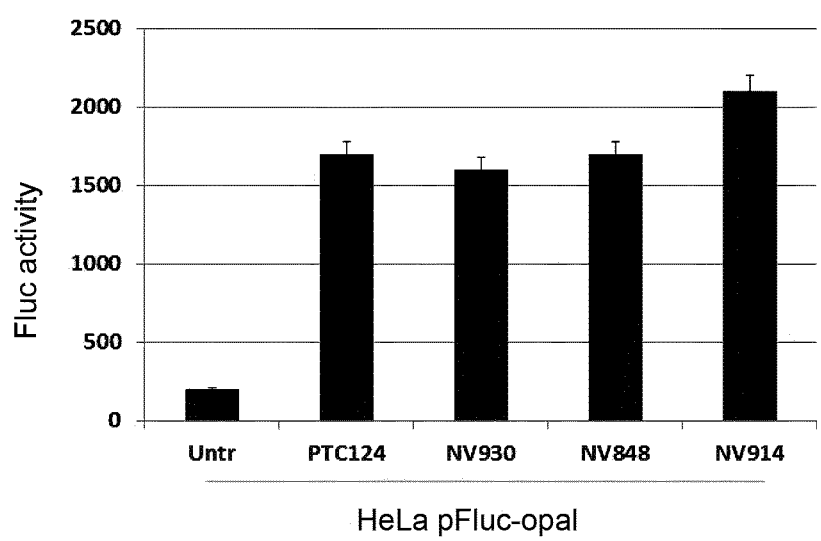
FIG. 2 shows a histogram showing luciferase (FLuc) activity after 24 h of exposition to ATALUREN and its analogues in HeLa FLuc-opal transfected cells.

To ascertain the effectiveness of the newly synthesized ataluren analogues in promoting the readthrough of premature termination codons was used the FLuc cell-based assay. To this aim HeLa cells were transfected transiently with the plasmids pFLuc-wild type (control) and pFLuc-opal (UGA stop mutation) (NIH Chemical Genomics Center, National Institutes of Health, Bethesda, USA). FLuc gene expression was then measured by luminescence. HeLa cells transfected with the pFluc-wild type plasmid showed high levels of luciferase activity confirming the functioning of the assay. pFluc-opal cells did not show any activity but, after 24 hours from transfection, they were treated, for additional 24 hours, with ataluren and 58 different ataluren analogues all at the same concentration of 12 µM. Following treatment a significant increase of luciferase activity, if compared to untreated, with: NV848, NV914, NV930 was observed as shown in FIG. 2.

To work in a cell system containing exclusively nonsense mutations and in particular the more representative CFTR nonsense mutation, the G542X, FRT cells were engineered with a vector expressing nsCFTR (nonsense). To this aim, Site Directed Mutagenesis of the full-length CFTR cDNA cloned in the pTracer-Zeocin (pTCF-wild type) vector (Gaslini Hospital Genova, Italy) was performed (CFTR DNA available at NCBI Reference Sequence: NG_016465.4). To substitute the Glicine 542 coding codon GGA with a stop codon, was introduced a single nucleotide mutation. The first guanine of the codon, position 1624 of the cDNA, was changed in a thymine to introduce an opal nonsense mutation. We amplified the plasmid harbouring cDNA with the following primers:

g1624tup (reverse)
SEQ ID NO. 1:
5'-tgattccaccttctcaaagaactatattgtctttctctgcaaac-3' g1624tdw (forward)
SEQ ID NO.2:
5'-gtttgcagagaaagacaatatagttctttgagaaggtggaatca-3'

Figure 3:
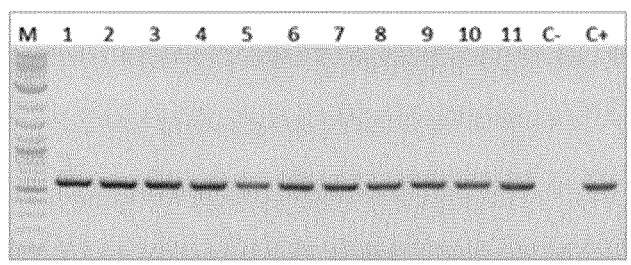
FIG. 3 shows a colony PCR.

Treatment with DpnI restriction enzyme (target: 5'Gm6ATC3') removed methylated parental DNA (isolated from dam+ *E. coli*). Newly synthesized plasmids were transformed into XL1-Blue competent cells. We obtained 11 colonies, all confirmed to bring the pTracer-CFTR plasmid by colony PCR performed with two primers perfectly annealing to the template at 52° C.: SEQ ID NO. 3: 5'-ctaatgagaaacggtgtaag-3' CFTRup2 reverse primer and: SEQ ID NO. 4: 5'-ggtgattatgggagaactgg-3' CFTRdw1 forward primer, as shown in FIG. 3.

clone1 was selected for further characterization by "selective PCR". A forward primer SEQ. ID NO. 5 5'-gagaaagacaatatagttcttt-3' CFTR1624opaldw, with 3' termini matching only to mutant nucleotide allows amplification of the corresponding mutant target DNA and not of wild type DNA, when the right selective PCR conditions are used. We performed reactions with a thermostable DNA polymerase lacking 3' to 5' proofreading activity (DyNAzyme™ II DNA Polymerase), identical amount of purified plasmid DNA, either wild type or mutagenized, and the reverse primer SEQ. ID. NO. 3: 5' ctaatgagaaacggtgtaag 3' CFTRup2.

To distinguish between mutant and wild type DNA, was used a gradient thermocycler and the following primer annealing temperatures: 44, 46, 48, 50 and 52° C. Positive controls (C+) were included where the same DNAs were amplified with the CFTRup2/CFTRdw1 primers (annealing T 52° C.)

Figure 4:
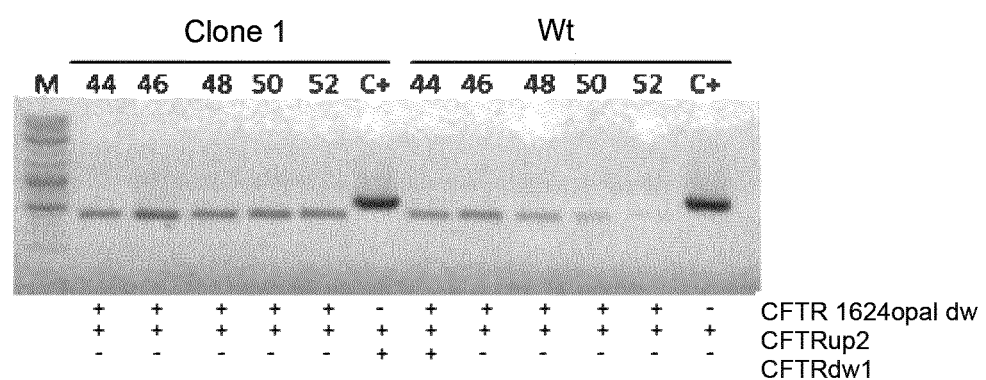
FIG. 4 shows a selective PCR.

A DNA fragment of the correct size was amplified where expected, either in clone-1 or wild type DNA and in positive controls, as shown in FIG. 4.

In the case of Clone1 when the selective forward primer was used, the amplification efficiency was the same at any annealing T. In the case of wild type DNA, amplification product amount decreased as the T raised, until it became almost undetectable at 52° C., thus suggesting that Clone1 was positive to mutagenesis. Successful mutagenesis was finally confirmed by sequencing (BRM genomics, Padova, Italy).

Figure 5:
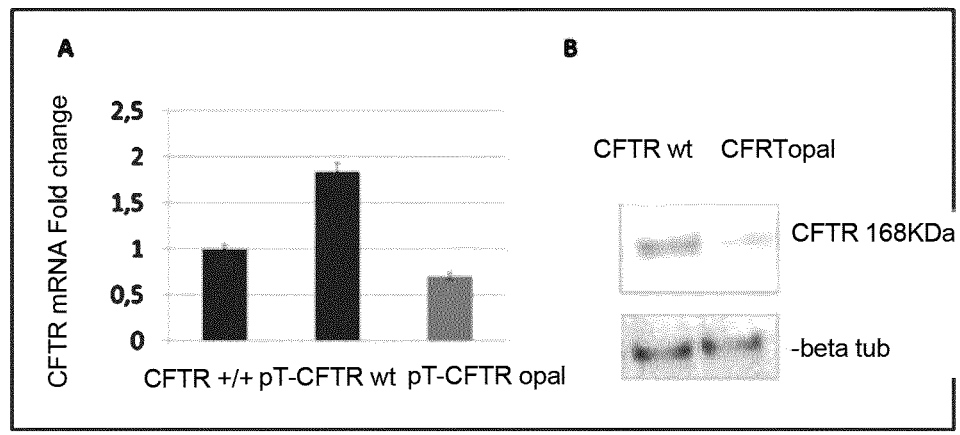
FIG. 5 shows in panel A the real time RT-PCR to visualize CFTR expression after Zeocin selection in FRT cells; in panel B the western blot analysis to detect CFTR protein in FRT transfected cells (CFTR wild type and nsCFTR (opal). Beta-tubulin was used as control for the protein loading.
Figure 6:
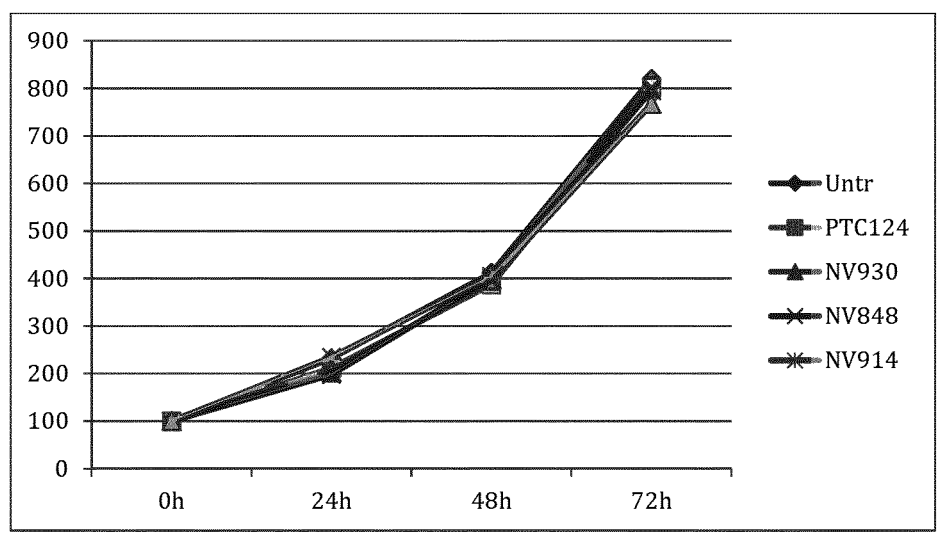
FIG. 6 shows the cell viability test for our compounds compared to Ataluren.

To further evaluate the efficacy of NV914, NV848, NV930, FRT cells were transfected with the pTRACER vectors containing either the wild type CFTR or the nsCFTR (G542X-opal) cDNA and selected by Zeocin resistance. The advantage of the use of these cells is that they don't express cAMP dependent channels (as CFTR) or CFTR protein. The expression of the human CFTR wild type and nsCFTR (G542X-opal) in transfected FRT cells was evaluated by qRT-PCR and Western blot, as shown in FIG. 5.

The same FRT cells were then treated with NV914, NV848, NV930 (12 μM), and ATALUREN (12 μM) (as positive control) for 24 hours and the expression of the human CFTR wild type and nsCFTR(G542X-opal) was again evaluated by immunofluorescence analysis. Immunofluorescence microscopy images allow to visualize CFTR localization at the cell membrane suggesting the occurrence of translation readthrough and proper localization also in this cell type after treatment.

The results showed that the exposition of nsCFTR (G542X-opal) FRT cells to the compounds induced CFTR full-length expression and membrane localization, in particular for compounds NV930 and NV914.

Figure 7:
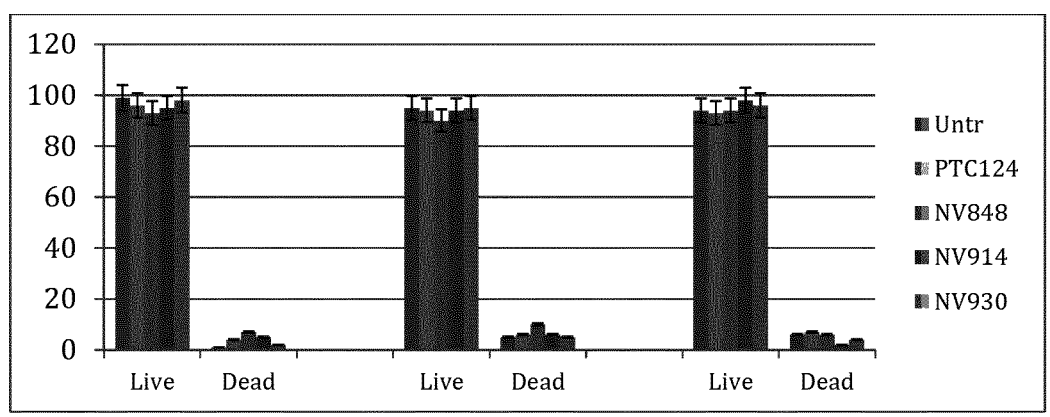
FIG. 7 shows the percentages of dead cells and proliferating cells after treatment with 12 μM compounds and 12 μM ataluren.

HeLa cells were used to determine the possible cytotoxic effects of our compounds and the impact on cell proliferation. In FIG. 7 are reported the percentages of dead cells and proliferating cells after treatment with 12 μM compounds and 12 μM ATALUREN. The results showed that the compounds and ATALUREN induce alight increase in dead cells at 24 h (ATALUREN: 4%; NV848: 7; NV914: 5; NV930: 2) and 72 h (ATALUREN: 7%; NV848: 6; NV914: 2; NV930: 4 that was constant in the time. Was observed that HeLa cells proliferate as untreated cells when treated daily (every 24 h) for 10 days with our compounds.

In the attempt to predict absorption, distribution, metabolism, and excretion (ADME) for the compounds, these was submitted to Qikprop calculations.

Regarding ADME predictions the final result is expressed in terms of #stars, Number of property or descriptor values that fall outside the 95% range of similar values for known drugs large number of stars suggests that a molecule is less drug-like than molecules with few stars. The following properties and descriptors are included in the determination of #stars: MW, dipole, IP, EA, SASA, FOSA, FISA, PISA, WPSA, PSA, volume, #rotor, donorHB, acceptHB, glob, QPpolrz, QP log PC16, QP log Poct, QP log Pw, QP log Po/w, log S, QPLogKhsa, QP log BB, #metabol, as shown in the following Table 4 wherein all the calculated values for the compounds were compared with the calculated values for ataluren.

TABLE 4

| molecule | #stars (0-5) | MW (130-725) | Dipole (1.0-12.5) | IP(eV) (7.9-10.5) | EA(eV) (−0.9-1.7) | SASA (300-1000) | FOSA (0-750) | FISA (7.0-330) |
|---|---|---|---|---|---|---|---|---|
| PTC124 | 1 | 284.246 | 1.915 | 9.725 | 1.341 | 520.123 | 0 | 154.63 |
| NV 0848 | 0 | 141.129 | 4.608 | 9.956 | 0.619 | 345.739 | 178.407 | 146.87 |
| NV 0914 | 3 | 445.176 | 4.123 | 10.476 | 2.313** | 591.639 | 0 | 101.555 |
| NV 0930 | 1 | 218.212 | 2.767 | 9.953 | 1.238 | 478.415 | 140.814 | 115.047 |

| molecule | PISA (0-450) | WPSA (0-175) | PSA (7-200) | Volume (500-2000) | #rotor (0-15) | donorHB (0-6) | acceptHB (2-20) | Glob (0.75-0.95) |
|---|---|---|---|---|---|---|---|---|
| PTC124 | 333.429 | 32.065 | 85.12 | 866.815 | 1 | 1 | 5 | 0.8453 |
| NV 0848 | 20.461 | 0 | 80.17 | 518.729 | 1 | 1 | 5.5 | 0.90305 |
| NV 0914 | 117.841 | 372.242 | 71.024 | 1002.895 | 2 | 1 | 5.5 | 0.81899 |
| NV 0930 | 222.554 | 0 | 74.776 | 764.735 | 2 | 0 | 5 | 0.84534 |

| molecule | QPpolrz (13-70) | QPlogPC16 (4-18) | QPlogPoct (8-35) | QPlogPw (4-45) | QPlogPo/w (−2.0-6.5) | QPlogKhsa (−1.5-1.5) | QPlogBB (−3.0-1.2) | #metab (1-8) |
|---|---|---|---|---|---|---|---|---|
| PTC124 | 31.078 | 9.63 | 14.802 | 10.471 | 2.6 | −0.174 | −0.861 | 0 |
| NV 0848 | 14.159 | 4.306 | 9.061 | 8.351 | −0.567 | −0.884 | −0.697 | 1 |
| NV 0914 | 33.823 | 6.818 | 17.188 | 9.207 | 4.127 | 0.192 | 0.347 | 0 |
| NV 0930 | 25.292 | 7.491 | 10.819 | 7.651 | 1.733 | −0.584 | −0.63 | 0 |

In table 4 MW, molecular weight; IP, PM3 calculated ionization potential (negative of HOMO energy); EA, PM3 calculated electron affinity (negative of LUMO energy); SASA, Total solvent accessible surface area (SASA) in square angstroms using a probe with a 1.4 Å radius; FOSA, Hydrophobic component of the SASA (saturated carbon and attached hydrogen); FISA, Hydrophilic component of the SASA (SASA on N, O, H on heteroatoms, carbonyl C); PISA, (carbon and attached hydrogen) component of the SASA; WPSA, Weakly polar component of the SASA (halogens, P, and S); Volume, Total solvent-accessible volume in cubic angstroms using a probe with a 1.4 Å radius; #rotor, number of rotatable bonds; donorHB, number of h-bond donor, accptHB, number of H-bond acceptor; glob, Globularity descriptor, (4=2) ´ (SASA), where r is the radius of a sphere with a volume equal to the molecular volume; QPpolrz, Predicted polarizability in cubic angstroms, QP log PC16, Predicted hexadecane/gas partition coefficient; QP log Poct, Predicted octanol/gas partition coefficient; QP log Pw, Predicted water/gas partition coefficient; QP log Po/w, Predicted octanol/water partition coefficient; QP log Khsa, Prediction of binding to human serum albumin; QP log BB, Predicted brain/blood partition coefficient; #metab, Number of likely metabolic reactions.

Furthermore, the compounds respect the Lipinski's rule of five, and they have a predicted human oral absorption between 70 and 100%.

It was also evaluated the production of FRT cells expressing nonsense-CFTR (nsCFTR) and the CFTR expression and functionality after treatment with NV848, NV914 and NV930.

FRT cells transfected with a pTracer nsCFTR-G542X-opal vector the treated with NV848, NV914, NV930 (12 μM), and ATALUREN (12 μM) as positive control, for 24 hours and the expression of the human CFTR wild type and nsCFTR (nsCFTR-G542X-opal) was evaluated by immunofluorescence analysis.

In details, immunofluorescence analysis was used to detect the CFTR protein following the readthrough of the UGA stop codon in nsCFTR(opal) FRT cells untreated, treated with G418 as positive contro) and with PTC124 and NV848, Nv914, NV930 for 24 h. CFTR protein was revealed by a specific antibody targeting its first external portion and a secondary antibody (SC2092-red). Nuclei (blue) were DAPI stained.

Immunofluorescence microscopy images allowed to visualize CFTR localization at the cell membrane suggesting the occurrence of translation readthrough and proper localization also in this cell type after treatment, and the results showed that the exposition of nsCFTR(G542X-opal) FRT cells to the NV848, NV914, NV930 compounds induced the CFTR full-length expression and membrane localization.

Moreover, by Western blot analysis was detected the amount of CFTR protein after translation readthrough in nsCFTR(G542X-opal) FRT cells treated with NV848, NV914, NV930 (12 μM). In details, Western blot analysis was used to detect CFTR protein in bronco-epithelial BE (cells and in transfected FRT cells (FRT-CFTR(gG542X-opal) untreated and treated with PTC124 and and NV848, NV914, NV930, for 24 hours and β-tubulin was used as control for the protein loading.

To ascertain the functionality of the re-expressed CFTR protein, produced after exposure to the compounds, a quench-EYFP assay was performed. This assay is based on iodide-mediated quenching rates of an ectopically expressed mutant form of the Yellow fluorescent protein (YFP). To this aim, nsCFTR(G542X-opal) FRT-cells were transfected with the plasmid pCDNA3.1 EYFP (M148Q; I152L) and selected for the resistance to the G418 antibiotic. Cells were plated in a 6 well plate one day before the experiment, they were stimulated with forskolin (20 μM) for 20 min and placed in a buffer containing iodide (PBS1× similar buffer, NaCl is replaced by equimolars of NaI). Changes in fluorescence intensity were monitored by a Zeiss fluorescence microscope and the images were recorded every 1.5 s with a CCD digital camera (AxioCam, Zeiss). The same analysis was performed by measuring the changes in fluorescence intensity by a fluorimeter confirming the activity of the CFTR channel in these cells.

FRT cells were also engineered with a vector expressing nsCFTR (nonsense). To this aim, Site 15 Directed Mutagenesis of the full-length CFTR cDNA cloned in the pTracer Zeocin (pTCF-wild type) vector (provided by Gaslini Hospital Genova, Italy) was performed, the CFTR DNA is available at NCBI Reference Sequence NG_016465.4. With the aim of introducing in the CFTR cDNA single base mutations c1654t or c1657t to convert, respectively, Glycin 552 (caa>taa ochre) or Arginine 553 (cga>tga opal) in nonsense codons, site-directed mutagenesis of the full-length cDNA cloned in the pTracer Zeocin (pTCF-wild type) vector (provided by Gaslini Hospital Genova, Italy) was performed (CFTR DNA available at NCBI Reference Sequence: NG_016465.4). The pTCF-wild type vector was amplified by PCR with the following primers:

```
Q552X och dw forward,
                                    SEQ. ID No. 6
gaatcacactgagtggaggttaacgagcaagaatttcttta Q552X och up reverse
                                    SEQ. ID No. 7
taaagaaattcttgctcgttaacctccactcagtgtgattc
or R553X op dw forward,
                                    SEQ. ID No. 8
aatcacactgagtggaggtcaatgagcaagaatttctttag R553X op up reverse
                                    SEQ. ID No. 9
ctaaagaaattcttgctcattgacctccactcagtgtgatt
```

Treatment with DpnI restriction enzyme (target: 5'Gm6ATC3') removed methylated parental DNA (isolated from dam+ *E. coli*). Newly synthesized plasmids were transformed into XL1-Blue competent cells. We obtained 11 colonies from Q552X reaction and 12 from R553X. All were confirmed to bring the pTracer-CFTR plasmid by colony PCR, performed with two primers perfectly annealing to the template at 56° C.:

```
CFTRup2 reverse primer
                                   SEQ. ID No. 10
Ctaatgagaaacggtgtaag
and CFTRdw1 forward primer
                                   SEQ. ID No. 11
ggtgattatgggagaactgg
```

Q552X clone 1 and R553X clone 18 were selected for further characterization by selective PCR, based on the use of the CFTRup2 reverse primer SEQ. ID No. 9 paired with the following selective forward primers:

```
c1654tdw for Q552X
                                   SEQ. ID No. 12
aatcacactgagtggaggtt
or c1657tdw for R553X
                                   SEQ. ID No. 13
cacactgagtggaggtcaat
```

They harbor a 3' termini matching only to mutant nucleotides, which allow the amplification of the mutant target DNA and not of wt DNA by a thermostable DNA polymerase lacking 3' to 5' proofreading activity (DyNAzyme™ II DNA Polymerase). Primer annealing temperatures ranging from 48 to 56° C. were used. Amplification efficiency, of mutant clones 1 and 18 was the same at any annealing T (Ta) while in the case of wt template DNA, it decreased as the Ta raised (380 bp amplicon became almost undetectable at 56° C.). This suggested that both clones were positive to mutagenesis. A DNA fragment of 608 bp was amplified in positive controls, as expected. Successful mutagenesis was confirmed by sequencing (BRM genomics):

To further evaluate the efficacy of NV848, NV914 and NV930 FRT cells were transfected with the pTracer vectors containing either the WT-CFTR (CFTRWT) or the R553X-CFTR and the Q552X-CFTR (nsCFTR-R553X-opal, nsCFTR-Q552X ochre) human cDNA and selected by Zeocin resistance. The expression of the CFTRWT and nsCFTR CFTR (nsCFTR-R553X-opal, nsCFTR-Q552X ochre) in transfected FRT cells was evaluated by qRT-PCR. The nsCFTR-Q552X ochre, nsCFTR-R553X-opal FRT transfected cells were treated with NV848, (12 µM), and ATALUREN (12 µM) as positive control, for 24 hours and the expression of the human CFTR was evaluated by immunofluorescence analysis. Immunofluorescence microscopy images showed that the exposition of the nsCFTR-R553X-opal, nsCFTR-Q552X ochre FRT cells to the NV848, NV914, NV930 compounds induced the CFTR full-length expression and membrane localization.

The invention claimed is:

1. A compound consisting of 2,3,4,5,6-pentafluoro-N-(5-(perfluorophenyl)-1,2,4-oxadiazol-3-yl)benzamide.

2. A method for the preparation of the compound of claim 1, the method comprising acylation with perfluorobenzoyl chloride of amine 2 according to the following reaction:

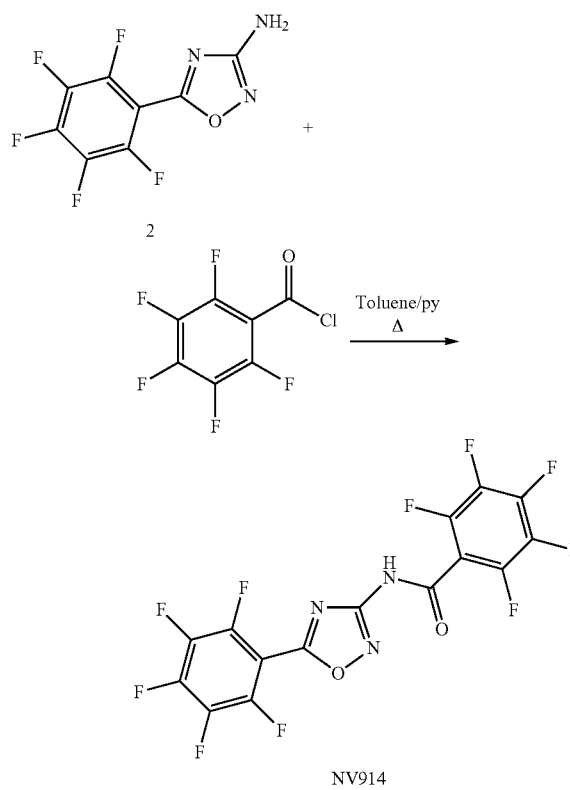

3. A pharmaceutical composition comprising a pharmacologically effective amount of the compound of claim 1 or a prodrug thereof and pharmaceutically acceptable excipients.

4. A method for treating a disease caused by nonsense mutations comprising administering the pharmaceutical composition of claim 3 to a patient affected by a disease caused by nonsense mutations and in the need thereof.

5. A method for treating a disease caused by nonsense mutations comprising administering the compound of claim 1 to a patient affected by a disease caused by nonsense mutations and in the need thereof.

6. A pharmaceutical compositions comprising a pharmacologically effective amount of a compound selected from the group consisting of: 2,3,4,5,6-pentafluoro-N-(5-perfluorophenyl)-1,2,4-oxadiazol-3- yl)benzaminde, N-(5-methyl-1,2,4-oxadiazol-3-yl)acetamide, ethyl 5-phenyl-1,2,4-oxadiazole-3-carboxylate, a prodrug thereof, or a mixture thereof.

7. A method of treating a disease caused by nonsense mutation comprising administering the pharmaceutical composition of claim 6 to a patient affected by the disease caused by nonsense mutations and in the need thereof.

8. A method of treating a disease caused by nonsense mutation comprising administering a pharmacologically effective amount of a compound selected from the group consisting of: 2,3,4,5,6-pentafluoro-N-(5-(perfluorophenyl)-1,2,4-oxadiazol-3-yl)benzamide, N-(5-methyl-1,2,4-oxadiazol-3-yl)acetamide, ethyl 5-phenyl-1,2,4-oxadiazole-3-carboxylate, or mixture thereof to a patient affected by the disease caused by nonsense mutations and in the need thereof.

\* \* \* \* \*

```
                        SEQUENCE LISTING

<160> NUMBER OF SEQ ID NOS: 13

<210> SEQ ID NO 1
   <211> LENGTH: 44
   <212> TYPE: DNA
   <213> ORGANISM: Artificial Sequence
   <220> FEATURE:
   <223> OTHER INFORMATION: Synthetic

<400> SEQUENCE: 1
tgattccacc ttctcaaaga actatattgt ctttctctgc aaac              44

<210> SEQ ID NO 2
   <211> LENGTH: 44
   <212> TYPE: DNA
   <213> ORGANISM: Artificial Sequence
   <220> FEATURE:
   <223> OTHER INFORMATION: Synthetic

<400> SEQUENCE: 2
gtttgcagag aaagacaata tagttctttg agaaggtgga atca              44

<210> SEQ ID NO 3
   <211> LENGTH: 20
   <212> TYPE: DNA
   <213> ORGANISM: Artificial Sequence
   <220> FEATURE:
   <223> OTHER INFORMATION: Synthetic

<400> SEQUENCE: 3
ctaatgagaa acggtgtaag                                         20

<210> SEQ ID NO 4
   <211> LENGTH: 20
   <212> TYPE: DNA
   <213> ORGANISM: Artificial Sequence
   <220> FEATURE:
   <223> OTHER INFORMATION: Synthetic

<400> SEQUENCE: 4
ggtgattatg ggagaactgg                                         20

<210> SEQ ID NO 5
   <211> LENGTH: 22
   <212> TYPE: DNA
   <213> ORGANISM: Artificial Sequence
   <220> FEATURE:
   <223> OTHER INFORMATION: Synthetic

<400> SEQUENCE: 5
gagaaagaca atatagttct tt                                      22
```

<210> SEQ ID NO 6
<211> LENGTH: 41
<212> TYPE: DNA
<213> ORGANISM: Artificial Sequence
<220> FEATURE:
<223> OTHER INFORMATION: Synthetic

<400> SEQUENCE: 6
gaatcacact gagtggaggt taacgagcaa gaatttcttt a                41

<210> SEQ ID NO 7
<211> LENGTH: 41
<212> TYPE: DNA
<213> ORGANISM: Artificial Sequence
<220> FEATURE:
<223> OTHER INFORMATION: Synthetic

<400> SEQUENCE: 7
taaagaaatt cttgctcgtt aacctccact cagtgtgatt c                41

<210> SEQ ID NO 8
<211> LENGTH: 41
<212> TYPE: DNA
<213> ORGANISM: Artificial Sequence
<220> FEATURE:
<223> OTHER INFORMATION: Synthetic

<400> SEQUENCE: 8
aatcacactg agtggaggtc aatgagcaag aatttcttta g                41

<210> SEQ ID NO 9
<211> LENGTH: 41
<212> TYPE: DNA
<213> ORGANISM: Artificial Sequence
<220> FEATURE:
<223> OTHER INFORMATION: Synthetic

<400> SEQUENCE: 9
ctaaagaaat tcttgctcat tgacctccac tcagtgtgat t                41

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
ctaatgagaa acggtgtaag                                        20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
ggtgattatg ggagaactgg                                        20

<210> SEQ ID NO 12
<211> LENGTH: 20
<212> TYPE: DNA
<213> ORGANISM: Artificial Sequence
<220> FEATURE:
<223> OTHER INFORMATION: Synthetic

```
<400> SEQUENCE: 12
aatcacactg agtggaggtt                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
cacactgagt ggaggtcaat                                               20
```